US012376923B2

(12) United States Patent
Steger et al.

(10) Patent No.: US 12,376,923 B2
(45) Date of Patent: Aug. 5, 2025

(54) SYSTEMS AND METHODS FOR STERILIZATION AND STORAGE OF A STERILIZED TELEOPERATED COMPONENT

(71) Applicant: Intuitive Surgical Operations, Inc., Sunnyvale, CA (US)

(72) Inventors: John Ryan Steger, Los Gatos, CA (US); Daniel H. Gomez, Los Gatos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1105 days.

(21) Appl. No.: 17/283,648

(22) PCT Filed: Oct. 14, 2019

(86) PCT No.: PCT/US2019/056062
§ 371 (c)(1),
(2) Date: Apr. 8, 2021

(87) PCT Pub. No.: WO2020/081429
PCT Pub. Date: Apr. 23, 2020

(65) Prior Publication Data
US 2021/0386493 A1    Dec. 16, 2021

Related U.S. Application Data

(60) Provisional application No. 62/745,571, filed on Oct. 15, 2018.

(51) Int. Cl.
*A61B 34/35*   (2016.01)
*A61B 17/00*   (2006.01)
(Continued)

(52) U.S. Cl.
CPC .............. *A61B 34/35* (2016.02); *A61B 50/30* (2016.02); *A61L 2/26* (2013.01);
(Continued)

(58) Field of Classification Search
CPC ........... A61B 2017/00221; A61B 2017/00725; A61B 2017/00212
See application file for complete search history.

(56) References Cited

U.S. PATENT DOCUMENTS 5,281,400 A    1/1994  Berry, Jr.
6,595,979 B1 *  7/2003  Epstein ............. A61M 5/14566
                                                    604/522

(Continued)

FOREIGN PATENT DOCUMENTS

CN    205569360 U    9/2016
CN    207709451 U    8/2018
(Continued)

OTHER PUBLICATIONS

International Preliminary Report on Patentability for Application No. PCT/US2019/056062, mailed on Apr. 29, 2021, 09 pages.

(Continued)

*Primary Examiner* — Wen W Huang
(74) *Attorney, Agent, or Firm* — Haynes & Boone, LLP.

(57) ABSTRACT

A system is provided including a reclosable storage container comprising an interior sterile environment. The system also includes a sterile teleoperated component of a teleoperated surgical manipulator assembly in the interior sterile environment. A communications interface enables communication between a device outside the storage container and the component inside the storage container. A viewing window allows the stored component to be seen through the storage container. Multiple storage containers can be moved and stored. In an operating room, the storage (Continued)

container is opened, and the component is removed and assembled into the teleoperated surgical assembly.

20 Claims, 8 Drawing Sheets

(51) Int. Cl.
*A61B 50/30* (2016.01)
*A61L 2/26* (2006.01)
*H04M 1/72415* (2021.01)
(52) U.S. Cl.
CPC ............... *H04M 1/72415* (2021.01); *A61B 2017/00221* (2013.01); *A61B 2017/00725* (2013.01); *A61L 2202/14* (2013.01)

(56) References Cited

U.S. PATENT DOCUMENTS

| | | | |
|---|---|---|---|
| 8,323,271 B2 | 12/2012 | Humayun et al. | |
| 9,848,827 B1 | 12/2017 | LaBorde | |
| 9,887,562 B2 | 2/2018 | Racenet et al. | |
| 2003/0069543 A1* | 4/2003 | Carpenter | A61M 25/0084 604/190 |
| 2004/0062692 A1 | 4/2004 | Lin et al. | |
| 2009/0187288 A1* | 7/2009 | Shimada | A61B 34/70 606/1 |
| 2010/0261961 A1 | 10/2010 | Scott et al. | |
| 2011/0224649 A1 | 9/2011 | Duane et al. | |
| 2012/0152289 A1 | 6/2012 | Smith et al. | |
| 2012/0253328 A1* | 10/2012 | Cunningham | A61B 18/1445 606/1 |
| 2014/0144799 A1 | 5/2014 | Praedel et al. | |
| 2017/0069199 A1 | 3/2017 | Magno et al. | |
| 2017/0143436 A1 | 5/2017 | Lathrop et al. | |
| 2017/0165837 A1* | 6/2017 | Asano | A61B 34/30 |
| 2018/0123365 A1 | 5/2018 | Racenet et al. | |
| 2018/0228351 A1 | 8/2018 | Scott et al. | |
| 2018/0333215 A1* | 11/2018 | Timm | B25J 9/0009 |
| 2018/0360553 A1* | 12/2018 | Nakanishi | A61B 34/37 |
| 2019/0167824 A1 | 6/2019 | Rhodes et al. | |
| 2019/0175294 A1 | 6/2019 | Abbott et al. | |
| 2019/0192245 A1 | 6/2019 | Abbott et al. | |
| 2019/0231461 A1 | 8/2019 | Steger et al. | |
| 2019/0290383 A1* | 9/2019 | Yaginuma | A61B 90/06 |
| 2020/0237939 A1* | 7/2020 | Henniges | G01K 17/02 |

FOREIGN PATENT DOCUMENTS

| | | |
|---|---|---|
| EP | 2881073 A1 | 6/2015 |
| WO | WO-2007142698 A2 | 12/2007 |
| WO | WO-2012085712 A1 | 6/2012 |
| WO | WO-2012148286 A1 | 11/2012 |
| WO | WO-2018039459 A1 | 3/2018 |
| WO | WO-2018053305 A1 | 3/2018 |
| WO | WO-2018075527 A1 | 4/2018 |

OTHER PUBLICATIONS

International Search Report and Written Opinion for Application No. PCT/US2019/056062, mailed on Mar. 3, 2020, 15 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEMS AND METHODS FOR STERILIZATION AND STORAGE OF A STERILIZED TELEOPERATED COMPONENT

CROSS-REFERENCE TO RELATED APPLICATIONS

This application is the U.S. national phase of International Application No. PCT/US2019/056062, filed Oct. 14, 2019, which designates the U.S. and claims priority to and the benefit of U.S. Provisional Application 62/745,571, filed Oct. 15, 2018, both of which are incorporated by reference herein in their entirety.

FIELD

The present disclosure is directed to systems and methods for sterilization and storing a sterilized teleoperated component.

BACKGROUND

Computer-assisted devices often include one or more movable manipulators operable to manipulate instruments for performing a task at a work site. The computer-assisted devices may include at least one movable manipulator for supporting a medical instrument, such as an image capturing device that captures images of the work site or a surgical instrument that may be used to manipulate or treat tissue at the surgical work site. A movable manipulator can include interconnected links that are coupled together by one or more actively controlled joints. The manipulator can include one or more passive joints that are not actively controlled and comply with movement of an actively controlled joint.

The computer-assisted devices can include industrial and recreational systems, and also medical robotic systems used in procedures for diagnosis, cosmetics, therapeutics, non-surgical treatment, surgical treatment, etc. As a specific example, computer-assisted devices include minimally invasive, computer-assisted, teleoperated surgical systems ("telesurgical systems") that allow a surgeon to operate on a patient from bedside or a remote location. Telesurgery is a general term for surgical systems in which the surgeon, rather than directly holding and moving all parts of the instruments by hand, uses some form of indirect or remote control, e.g., a servomechanism, or the like, to manipulate surgical instrument movements with at least partial computer assistance. The surgical instruments for such surgical systems can be inserted through minimally invasive surgical apertures or natural orifices to treat tissues at sites within the patient, often reducing the trauma generally associated with accessing a surgical worksite by open surgery techniques.

Computer-assisted devices may be sterilized prior to use in surgical procedures. Improved systems and methods are needed to sterilize one or more computer-assisted devices, store the sterile computer-assisted devices, and introduce the sterilized computer-assisted devices into a surgical environment, such as an operating room, in a sterile condition. Further, improved systems and methods are needed to determine whether the sterile computer-assisted devices are functioning properly or to gather other information from the sterile computer-assisted devices while maintaining sterility of the computer-assisted devices.

SUMMARY

Embodiments of the present disclosure are summarized by the claims that follow the description.

Consistent with some embodiments, a system is provided. The system includes a reclosable storage container comprising an interior sterile environment. The system further includes a sterile teleoperated component of a teleoperated surgical manipulator assembly in the interior sterile environment.

Consistent with other embodiments, a method includes performing a cleaning operation on a teleoperated component of a teleoperated surgical manipulator assembly used during a surgical procedure on a first patient, to produce a cleaned teleoperated component. The method further includes placing the cleaned teleoperated component into a storage container. The method further includes sterilizing the cleaned teleoperated component in the storage container and the storage container together to produce a sterilized teleoperated component in a sterile interior environment of the storage container.

Consistent with other embodiments, a method of evaluating a sterilized teleoperated component positioned within a sterile storage container is provided. The method includes establishing a communication through a wall of the sterile storage container to the sterilized teleoperated component. The method further includes, responsive to the communication, moving a mechanism of the sterilized teleoperated component.

Other embodiments include corresponding computer systems, apparatus, and computer programs recorded on one or more computer storage devices, each configured to perform the actions of the methods.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 1:
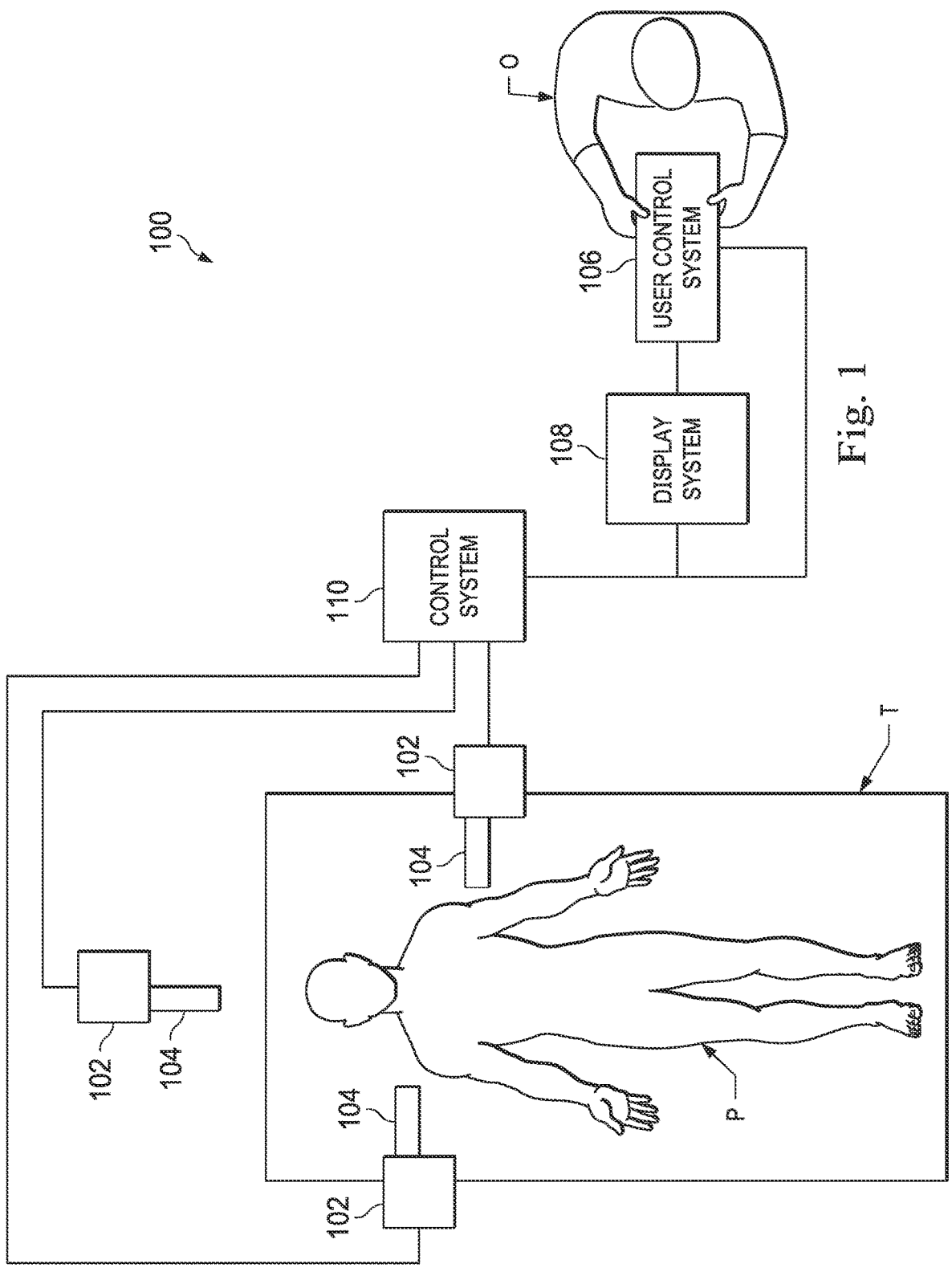
FIG. 1 is a simplified diagram of a computer-assisted, teleoperated system according to some embodiments.

Embodiments of the present disclosure and their advantages are described in the detailed description that follows. It should be appreciated that like reference numerals are used to identify like elements illustrated in one or more of the figures for purposes of illustrating but not limiting embodiments of the present disclosure.

DETAILED DESCRIPTION

In the following description, specific details describe some embodiments consistent with the present disclosure. Numerous specific details are set forth in order to provide a thorough understanding of the embodiments. It will be apparent to one skilled in the art, however, that some embodiments may be practiced without some or all of these specific details. The specific embodiments disclosed herein are meant to be illustrative but not limiting. One skilled in the art may realize other elements that, although not specifically described, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, components, and circuits have not been described in detail so as not to unnecessarily obscure aspects of the embodiments.

Further, specific words chosen to describe one or more embodiments and optional elements or features are not intended to limit the present disclosure. For example, spatially relative terms—such as "beneath", "over", "proximal", "distal", and the like—may be used to describe one element's or feature's relationship to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "beneath" other elements or features would then be "over" the other elements or features. Thus, the example term "beneath" can encompass both positions and orientations of over and beneath. A device may be otherwise oriented (e.g., rotated 90 degrees or at other orientations) and the spatially relative descriptors used herein interpreted accordingly. Likewise, descriptions of movement along (translation) and around (rotation) various axes include various special device positions and orientations. The combination of a body's position and orientation define the body's pose.

In addition, the singular forms "a", "an", and "the" are intended to include the plural forms as well, unless the context indicates otherwise. And the terms "comprises," "comprising," "includes," "has," and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components. The auxiliary verb "may" likewise implies that a feature, step, operation, element, or component is optional.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

A computer is a machine that follows programmed instructions to perform mathematical or logical functions on input information to produce processed output information. A computer includes a logic unit that performs the mathematical or logical functions, and memory that stores the programmed instructions, the input information, and the output information. The term "computer" and similar terms, such as "processor" or "controller" or "control system", are analogous.

Although some of the examples described herein refer to surgical procedures or instruments, or medical procedures and medical instruments, the techniques disclosed apply to non-medical procedures and non-medical instruments. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy), and performing procedures on human or animal cadavers. Further, these techniques can also be used for surgical and nonsurgical medical treatment or diagnosis procedures.

Further, although some of the examples presented in this disclosure discuss teleoperational robotic systems or remotely operable systems, the techniques disclosed are also applicable to computer-assisted systems that are directly and manually moved by operators, in part or in whole.

FIG. 1 is a simplified diagram of a computer-assisted, teleoperated system 100. In some embodiments, system 100 may be suitable for use in, for example, surgical, teleoperated surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic, general teleoperational, or robotic medical systems.

As shown in FIG. 1, system 100 generally includes a plurality of manipulator assemblies 102. Although three manipulator assemblies 102 are illustrated in the embodiment of FIG. 1, in other embodiments, more or fewer manipulator assemblies may be used. The exact number of manipulator assemblies will depend on the medical procedure and the space constraints within the operating room, among other factors. Multiple user control systems may be collocated or they may be positioned in separate locations. Multiple user control systems allow more than one operator to control one or more teleoperated manipulator assemblies in various combinations.

The manipulator assembly 102 is used to operate a medical instrument 104 (e.g., a surgical instrument or an image capturing device) in performing various procedures on a patient P. The medical instrument 104 is sterile prior to being used in the various procedures. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. In some embodiments, the manipulator assembly 102 may be mounted to or near an operating or surgical table T. In such embodiments, the manipulator assembly 102 may be mounted directly to the table T or to a rail coupled to the table T. In various other embodiments, the manipulator assembly 102 may be mounted to a manipulating system (e.g., a patient-side cart). The manipulating system may be separate from and spaced from the table T in the operating room. In such embodiments, the manipulating system may be independently movable relative to the table T. In other examples, the manipulator assembly 102 may be mounted to a ceiling of the operating room. In some additional examples, the manipulator assembly 102 may be mounted to one or more of a floor of the operating room or a wall of the operating room. In embodiments in which a plurality of manipulator assemblies 102 are employed, one or more of the manipulator assemblies 102 may support surgical instruments, and another of the manipulator assemblies may support an image capturing device such as a monoscopic or stereoscopic endoscope. In such embodiments, one or more of the manipulator assemblies 102 may be mounted to any structure or in any manner as described above. For example, one manipulator assembly 102 may be mounted to the table T and another manipulator assembly 102 may be mounted to a manipulating system. In other examples, an additional manipulator assembly 102 may be mounted to the ceiling of the operating room.

A user control system 106 allows an operator (e.g., a surgeon or other clinician, as illustrated in FIG. 1) to view the interventional site and to control manipulator assembly 102. In some examples, the user control system 106 is a surgeon console, which is usually located in the same room as the operating or surgical table T, such as at the side of a table on which patient P is located. However, it is to be understood that operator O can be located in a different room or a completely different building from patient P. User control system 106 generally includes one or more input devices for controlling manipulator assembly 102. The input devices may include any number of a variety of devices, such as joysticks, trackballs, data gloves, trigger-guns, hand-operated controllers, voice recognition devices, body motion or presence sensors, and/or the like. To provide operator O a strong sense of directly controlling medical instrument 104, the input devices may be provided with the same degrees of freedom as the associated medical instrument 104. In this manner, the input devices provide operator O with telepresence or the perception that the input devices are integral with medical instrument 104.

In some embodiments, the input devices may have more or fewer degrees of freedom than the associated medical instrument 104 and still provide operator O with telepresence. In some embodiments, the input devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Manipulator assembly 102 supports medical instrument 104 and may include a kinematic structure of one or more non-servo controlled links (e.g., one or more links that may be manually positioned and locked in place, generally referred to as a set-up structure), and/or one or more servo controlled links (e.g., one or more links that may be controlled in response to commands from a control system), and a manipulator. Manipulator assembly 102 may optionally include a plurality of actuators or motors that drive inputs on medical instrument 104 in response to commands from the control system (e.g., a control system 110). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to system 100 describing the rotation and orientation of the motor shafts. This position sensor data may be used to determine motion of the objects manipulated by the actuators. The manipulator assembly 102 may position its held instrument 104 so that a pivot point occurs at the instrument's entry aperture into the patient. The manipulator assembly 102 may then manipulate its held instrument so that the instrument may be pivoted about the pivot point, inserted into and retracted out of the entry aperture, and rotated about its shaft axis.

System 100 also includes a display system 108 for displaying an image or representation of the surgical site and medical instrument 104. Display system 108 and user control system 106 may be oriented so operator O can control medical instrument 104 and user control system 106 with the perception of telepresence. In some embodiments, medical instrument 104 may include a visualization system, which may include a viewing scope assembly that records a concurrent or real-time image of a surgical site and provides the image to the operator O and/or other operators or personnel through one or more displays of system 100, such as one or more displays of display system 108. The concurrent image may be, for example, a two or three dimensional image captured by an endoscope positioned within the surgical site. The visualization system may be implemented as hardware, firmware, software, or a combination thereof which interact with or are otherwise executed by one or more computer processors, which may include the processors of a control system 110.

In some examples, display system 108 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including, e.g., time-based or velocity-based information) images and/or as images from models created from the pre-operative or intra-operative image data sets.

System 100 may also include control system 110. Control system 110 includes at least one memory and at least one computer processor (not shown) for effecting control between medical instrument 104, user control system 106, and display system 108. Control system 110 also includes programmed instructions (e.g., a non-transitory machine-readable medium storing the instructions) to implement some or all the methods described in accordance with aspects disclosed herein, including instructions for providing information to display system 108. While control system 110 is shown as a single block in the simplified schematic of FIG. 1, the system may include two or more data processing circuits with one portion of the processing optionally being performed on or adjacent to manipulator assembly 102, another portion of the processing being performed at user control system 106, and/or the like. The processors of control system 110 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the robotic medical systems described herein. In one embodiment, control system 110 supports wireless communication protocols such as Bluetooth, IrDA, HomeRF, IEEE 802.11, DECT, and Wireless Telemetry.

In some embodiments, a communication is sent from the control system 110 to the manipulator assembly 102. Additionally, status information regarding testing of the manipulator assembly 102 may be sent from a sterile storage container (see 300 in FIG. 3) to the control system 110. This status information is used to optimize the performance of the system 100 by indicating an operational status of one or more components of the manipulator assembly 102. The status information may additionally be received by the operator O, a surgeon, and/or any other suitable personnel. The status information may also be received by a hospital information system, a patient information portal, a surgical information database, and/or any other suitable information system or database. In some embodiments, the status information is sent to a manufacturer of the manipulator assembly 102 to indicate whether the manipulator assembly 102 or any other component of the system requires maintenance. Communications between components of the manipulator assembly 102, the sterile storage container, and the control system 110 will be discussed in more detail below with respect to FIGS. 4E and 4F.

Movement of a manipulator assembly 102 may be controlled by the control system 110 so that a shaft or intermediate portion of instruments mounted to the manipulator assemblies 102 are constrained to safe motions through minimally invasive surgical access sites or other apertures. Such motion may include, for example, axial insertion of a shaft through an aperture site, rotation of the shaft about its axis, and pivotal motion of the shaft about a pivot point adjacent the access site. In some cases, excessive lateral motion of the shaft that might otherwise tear the tissues adjacent the aperture or enlarge the access site inadvertently is inhibited. Some or all of such constraint on the motions of the manipulator assemblies 102 at the access sites may be imposed using mechanical manipulator joint linkages that inhibit improper motions, or may in part or in full be imposed using data processing and control techniques. In some embodiments, control system 110 may receive force and/or torque feedback from medical instrument 104. Responsive to the feedback, control system 110 may transmit signals to user control system 106. In some examples, control system 110 may transmit signals instructing one or more actuators of manipulator assembly 102 to move medical instrument 104.

Figure 2:
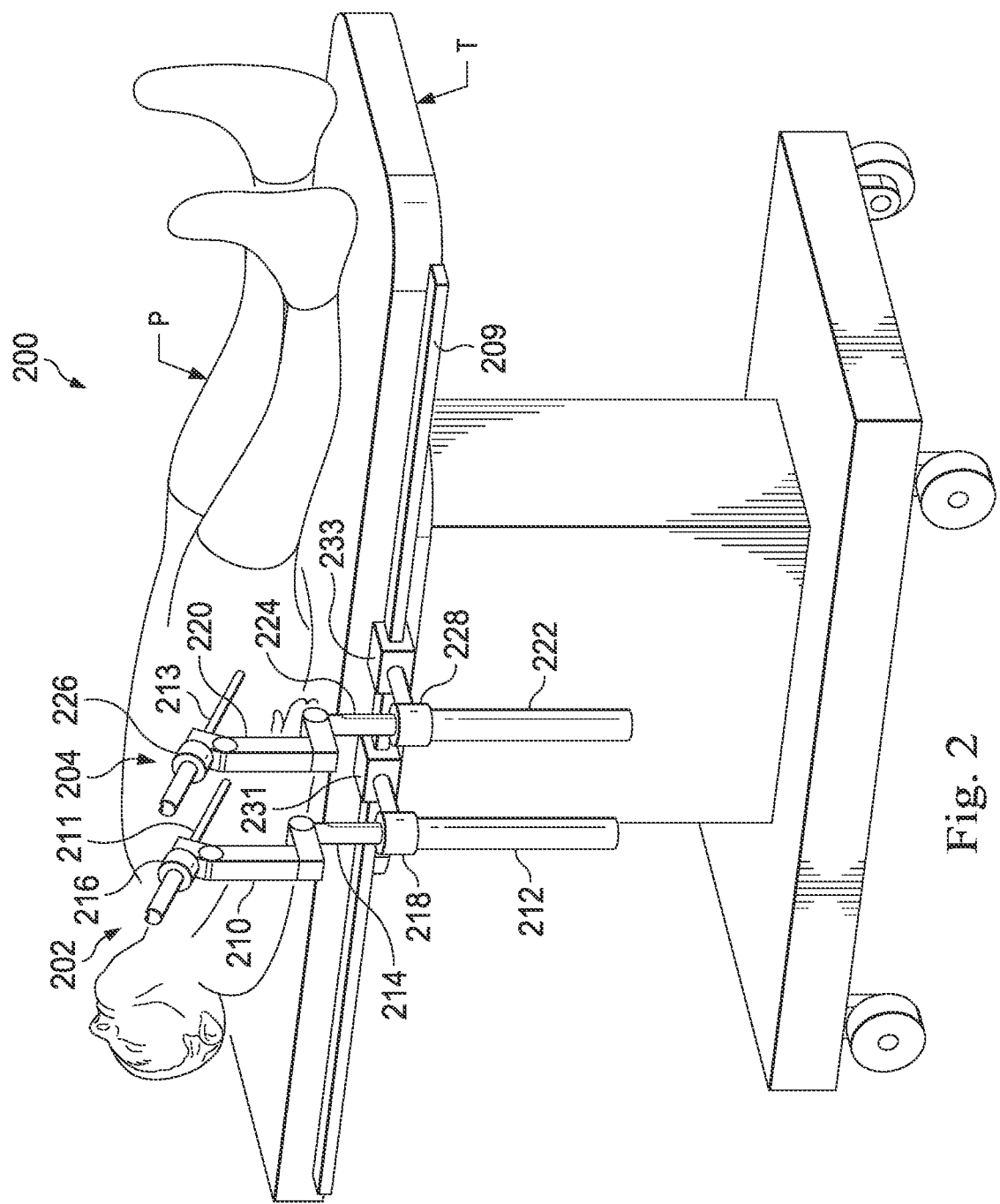
FIG. 2 is a perspective view of a patient coordinate space including a teleoperated surgical manipulator assembly mounted on a side of a surgical table according to some embodiments.

FIG. 2 is a perspective view of a patient coordinate space 200 including teleoperated surgical manipulator assemblies 202, 204 mounted on a side of a surgical table T according to some embodiments. In some embodiments, the manipulator assemblies 202, 204 may be used as manipulator assembly 102 in a medical procedure performed with system 100 and controlled by the control system 110. In some examples, the manipulator assemblies 202, 204 may be used in procedures involving traditional manually operated minimally invasive surgical instruments, such as manual laparoscopy. While only two manipulator assemblies 202, 204 are depicted, it is to be understood that more than two (e.g., three, four, five, six, and more than six) or fewer than two (e.g., one) manipulator assemblies can be included in some configurations.

In some embodiments, an equipment rail 209 is attached to the table T. The teleoperated surgical manipulator assemblies 202, 204 are coupled to the equipment rail 209 during the surgery. The manipulator assemblies 202, 204 may be coupled to the equipment rail 209 after being fully assembled, or the manipulator assemblies 202, 204 may be coupled to the equipment rail 209 before being fully assembled. In alternative embodiments, the equipment rail 209 may be attached to a manipulating system (e.g., a patient-side cart or a side table).

The manipulator assembly 202 may be operated to move an instrument 211 within the space 200, and the manipulator assembly 204 may be operated to move an instrument 213 within the space 200. The instruments 211, 213 are sterilized prior to use in a medical procedure.

The manipulator assembly 202 includes a manipulator 210, a link 214, and a drive unit 216. The manipulator assembly 204 includes a manipulator 220, a link 224, and a drive unit 226. The instrument 211 is coupled to the drive unit 216, and the instrument 213 is coupled to the drive unit 226. In some embodiments, the drive unit 216 is, for example, a standalone unit including a system of drive mechanisms (not shown, e.g., motors). The drive unit 216 may be operated to control motion of the instrument 211 in multiple degrees of freedom (DOFs) when the instrument 211 is mounted to the drive unit 216. The drive unit 226 is similarly configured for operation of the instrument 213. The drive unit 216 is coupled to the manipulator 210, and the drive unit 226 is coupled to the manipulator 220. The manipulator 210 is movably coupled to the link 214, and the manipulator 220 is movably coupled to the link 224. Any one or more of the components of the manipulator 210, the manipulator 220, the drive unit 216, and/or the drive unit 226 may be teleoperated. Thus, at least the manipulator 210, the manipulator 220, the drive unit 216, and/or the drive unit 226 are teleoperated components. The instruments 211, 213; the drive units 216, 226; the manipulators 210, 220; and the links 214, 224 are sterilized prior to use in a medical procedure. Additionally, one or more of the input devices (e.g., joysticks, trackballs, data gloves, trigger-guns, hand-operated controllers, voice recognition devices, body motion or presence sensors, and/or the like), which may be used for controlling manipulator assembly 102, may be sterilized prior to use in a medical procedure.

In some embodiments where the manipulator assembly 202 is mounted to a surgical table T, the manipulator assembly 202 is coupled to the table T by a coupling member 218 and a clamp 231. In some embodiments, the coupling member 218 is a joint (e.g., a ball joint, a spherical ball joint, a prismatic joint, a gimbal, and the like). The manipulator assembly 204 is coupled to the table T by a coupling member 228 and a clamp 233. Housing 212 is coupled to the coupling member 218, and housing 222 is coupled to the coupling member 228. In some examples, the manipulator assembly 202 includes the coupling member 218, the clamp 231, and the housing 212. In some examples, the manipulator assembly 204 includes the coupling member 228, the clamp 233, and the housing 222.

In some embodiments, the manipulator assembly 202 is coupled to the rail 209 of the operating table T by the clamp 231. The clamp 231 (which may be a support component and/or a support structure) kinematically supports the manipulator 210 and, therefore, the manipulator assembly 202 before, during, and/or after a surgical procedure. The clamp 231 may translate along the rail 209 to allow the position of the manipulator assembly 202 to be moved relative to the table T and the patient P.

As described in further detail below, one or more of the component parts of the input devices, the manipulator assembly 202, the coupling member 218, the clamp 231, and the housing 212 may be placed within an interior environment 420 of a storage container 300, 400 (see FIGS. 4A-4D) and sterilized together with the storage container 300, 400. In some embodiments, when removed from the interior environment 420, the clamp 231 is coupled to the table T via the rail 209. Alternatively, the clamp 231 may be coupled directly to the table T. The coupling member 218 is attached to the clamp 231. Accordingly, the clamp kinematically supports the manipulator 210 and, therefore, the manipulator assembly 202 before, during, and/or after a surgical procedure. In alternative embodiments, the clamp 231 may be coupled directly to the housing 212 or the link 214.

Figure 3:
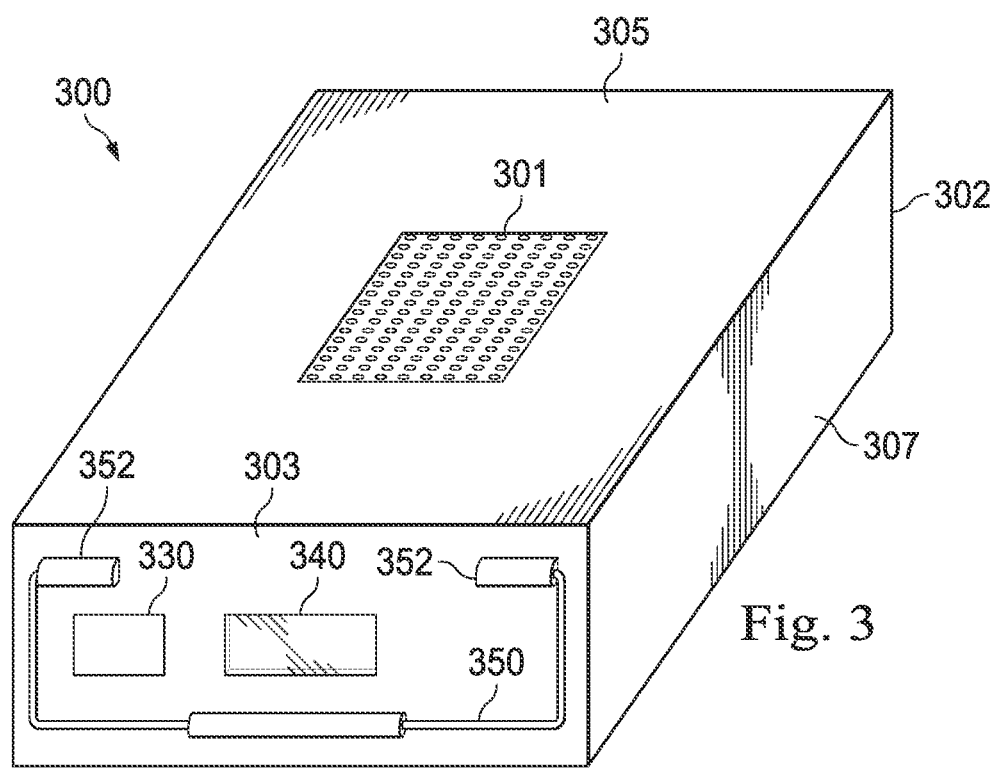
FIG. 3 is a perspective view of a reclosable storage container according to some embodiments.

FIG. 3 is a perspective view of a reclosable storage container 300 according to some embodiments. The storage container 300 includes an outer surface 302 defining an exterior of the storage container 300, a front wall 303, a back wall (not shown), a top 305, a bottom (not shown), and side walls 307. The storage container 300 also includes a communication interface 330 within the front wall 303, a viewing window 340 within the front wall 303, a vent 301 within the top 305, and a handle 350 attached to the front wall 303. In other examples, the communication interface 330 may be positioned within a back wall (not shown), the top 305, a bottom (not shown), and/or either one or both of the side walls 307. Similarly, the viewing window 340 may be positioned within the back wall (not shown), the top 305, the bottom (not shown), and/or either one or both of the side walls 307. Further, the vent 301 may be positioned within the back wall (not shown), the front wall 303, the bottom (not shown), and/or either one of the side walls 307. Additionally, the storage container 300 may include more than one vent 301. In various embodiments, the communication interface 330, the viewing window 340, and/or the handle 350 may be omitted.

In some embodiments, the manipulator assembly 202 is disassembled into component parts and one or more of the component parts are placed within an interior 420 (see FIG. 4A) of the storage container 300 such that one or more of the component parts of the manipulator assembly 202 are located within the storage container 300. For example, the component parts placed in the interior 420 of the storage container 300 may include the manipulator 210, the link 214, the coupling member 218, the housing 212, the drive unit 216, the clamp 231, input devices, and any other related components (e.g., a communication link or a kinematic arm). In alternative embodiments, one or only some of the component parts of the manipulator assembly 202 and/or input devices are placed within the interior 420 of the storage container 300. After the component parts are placed within the interior 420 of the storage container 300, the storage container 300 may be closed. The storage container 300 and the stored component parts may then be sterilized together. When the storage container 300 is closed, the storage container 300 may prevent microbes and other large molecules from entering the interior 420 while permitting sterilization of the interior 420 (e.g., via vent 301), as described in further detail below. The storage container 300, including the components of the manipulator assembly 202 in the interior 420 of the storage container 300, is sterilized using various methods. For example, an autoclave may be used. The autoclave sterilizes the storage container 300 and the components of the manipulator assembly 202 using a combination of steam, low and high pressure, and high temperature. After the sterilization process is complete, an operator (e.g., a sterilization technician) opens the autoclave and retrieves the storage container 300. The interior 420 of the storage container 300 and the components of the manipulator assembly 202 are now sterile and will remain sterile until the sterile interior 420 and the sterile components of the manipulator assembly 202 contact a non-sterile object or a non-sterile environment. In some embodiments, the storage container 300 is opened in a sterile environment. In such embodiments, the interior 420 of the storage container 300 and the components of the manipulator assembly 202 remain sterile even after the storage container 300 is opened. As other examples, the storage container 300, including the components of the manipulator assembly 202 in the interior 420 of the storage container 300, may be sterilized using a hydrogen peroxide sterilization method, a liquid chemical sterilization method, a low temperature, hydrogen peroxide gas plasma sterilization method, an ethylene oxide sterilization method, or any other suitable sterilization method.

In some embodiments, the outer surface 302, an inner surface 404 (see FIG. 4A), the front wall 303, the side walls 307, the back wall (not shown), the top 305, and the bottom (not shown)) of the storage container 300 are made of a material that can withstand a specific sterilization process (e.g., an autoclave sterilization process). For example, the walls and surfaces may be made of a material that can be sterilized under high pressure and high temperature. In other examples, the walls and surfaces may be made of a material that can be sterilized using chemicals, such as hydrogen peroxide or ethylene oxide, for example.

The walls and surfaces may also be made of a material that, in addition to being sterilizable under high pressure and high temperature, for example, allows for wireless signals to pass through the walls and surfaces. For example, a wireless signal may connect one or more components outside of the storage container 300 (e.g., the control system 110) to one or more components within the interior 420 of the storage container 300 (e.g., the manipulator 210). In such examples, the walls and surfaces may be made of plastic (such as polypropylene, polycarbonate, polysulfone, PEEK, polyphenylsulfone, polyetherimide, polyoxymethylene), ceramic, glass, or any other suitable material.

The vent 301 is a grouping of holes, which may be arranged in consecutive lines, in a symmetrical pattern, in a random order, etc. While the vent 301 is depicted within the top 305 of the storage container 300, it is to be understood that the vent 301 may be located within any other wall of the storage container 300, such as the front wall 303, one or more of the side walls 307, the back wall (not shown), or the bottom (not shown). In some embodiments, autoclave filter paper is placed behind the vent 301 and secured in place (i.e., such that the autoclave filter paper is positioned between the vent 301 and the interior environment 420 of the storage container 300). The autoclave filter paper may be secured in place with brackets, clasps, clips, or any other suitable connection method. The vent 301 and the autoclave filter paper behind it allow for steam to enter and/or exit the interior 420 of the storage container 300 during the sterilization process, such as the sterilization process in the autoclave. During the sterilization process, heat, pressure, and the steam extinguish any microbes within the interior 420 of the storage container 300. After the sterilization process is completed, the autoclave filter paper behind the vent 301 prevents microbes from entering the interior 420 of the storage container 300. In this way, the vent 301 and the filter paper prevent desterilization of the components within the interior 420 of the storage container 300. In alternative embodiments, the vent 301 may be a platform that is raised from the top 305, for example, of the storage container 300. In such embodiments, steam may enter and/or exit the interior 420 of the storage container 300 through a filtered gap between the vent 301 and the top 305 of the storage container 300. In further alternative embodiments, a sterilization wrap (which may be autoclave filter paper) is placed around the outside of the vent 301. For example, the entire storage container 300 may be wrapped (e.g., single wrapped, doubled wrapped, or wrapped any other suitable number of times) with sterilization wrap to create a sterile barrier between the interior 420 of the storage container 300 and the environment outside of the storage container 300.

The optional communication interface 330 connects one or more components outside of the storage container 300 (e.g., the control system 110) with one or more components in the interior 420 of the storage container 300 (e.g., the manipulator 210). The communication interface 330 may connect components by hardware or by non-contact based communication connections. In some examples, the one or more outside components and interior components may be connected through a mechanical connection, an optical connection, an electrical connection, an electromechanical connection, a wired connection, a wireless connection, an RFID connection, an inductive path connection, etc.

The optional viewing window 340 is used to view the components in the interior 420 of the storage container 300. An operator can look through the viewing window 340 and view the components in the interior 420 of the storage container 300. For example, the operator can look through the viewing window 340 to determine whether the manipulator 210 is responding to a communicated command, without opening the storage container 300 to view the manipulator 210. Thus, the operator can determine whether the manipulator 210 is functioning properly while maintaining sterility of the interior environment 420 and the manipulator 210.

The optional handle 350 may be used in combination with a similar optional handle on the opposite side of the storage container 300, such as the back wall (not shown). An operator uses the handle(s) 350 to pick up and hold the storage container 300. The handle(s) 350 may be used to hold the storage container 300 substantially level as the storage container 300 is carried from place to place. In some embodiments, the handle(s) 350 is connected to and swings on hinges 352 that are fixedly coupled to the front wall 303 of the storage container 300. In alternative embodiments, the handle(s) 350 may be connected to the front wall 303 of the storage container 300 by a screw connection, an adhesive connection, a welded connection, or any other suitable connection. In another aspect, one or more handles may be integrally formed on or in the outer surface 302 of the storage container 300.

In the embodiment of FIG. 3, the handle(s) 350 is connected to two hinges 352. In alternative embodiments, the handle(s) 350 may be connected to more than two hinges (e.g., three hinges, four hinges, or more than four hinges) or to less than two hinges (e.g., one hinge). While FIG. 3 shows the handle 350 attached to the front wall 303 of the storage container 300, it is to be understood that the handle 350 may be attached to any other wall of the storage container 300, such as the top 305, either one or both of the side walls 307, the back wall (not shown), or the bottom (not shown).

Figure 4A:
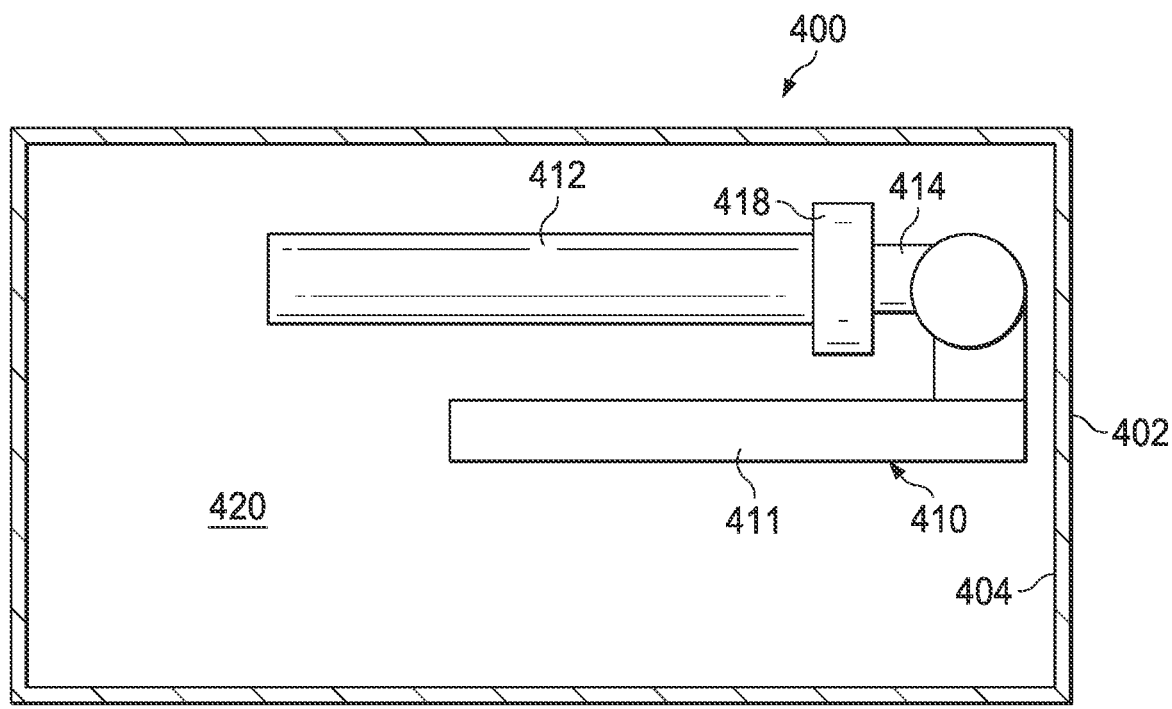
FIG. 4A is a top view of an interior of a reclosable storage container including a manipulator according to some embodiments.

FIG. 4A is a top view of the interior 420 of a storage container 400 including a manipulator 410 according to some embodiments. The storage container 400 is substantially similar to the storage container 300. The manipulator 410 is substantially similar to the manipulator 210. A link 414 is substantially similar to the link 214. The coupling member 418 is substantially similar to the coupling member 218, and the housing 412 is substantially similar to the housing 212.

The manipulator 410, the housing 412, the link 414, and the coupling member 418 are placed in the interior 420 of the storage container 400 before the storage container 400 is inserted into the autoclave. The storage container 400 is then closed and sterilized by undergoing a sterilization process in the autoclave. In this way, the storage container 400, the interior environment 420, and the components in the interior environment 420 are all sterilized together. After the sterilization process is completed, the interior contents are sterile, and the interior environment 420 is a sterile environment. The sterile interior environment 420 remains sterile until the sterile interior environment 420 contacts a non-sterile object or a non-sterile environment (e.g., the interior 420 remains sterile while the container 400 remains closed). The sterile interior environment 420 allows the sterile components inside the storage container 400 to remain sterile as they are stored for use and transported to an operating room for use during surgery.

Figure 4B:
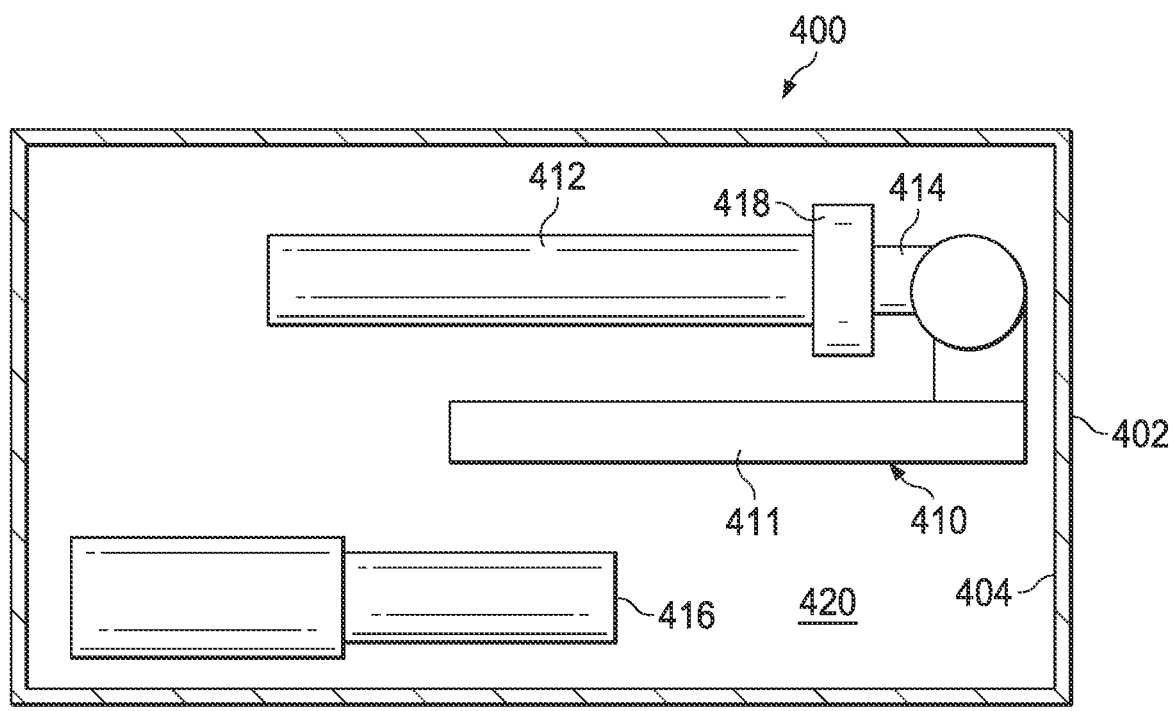
FIG. 4B is a top view of an interior of a reclosable storage container including a drive unit according to some embodiments.
Figure 4C:
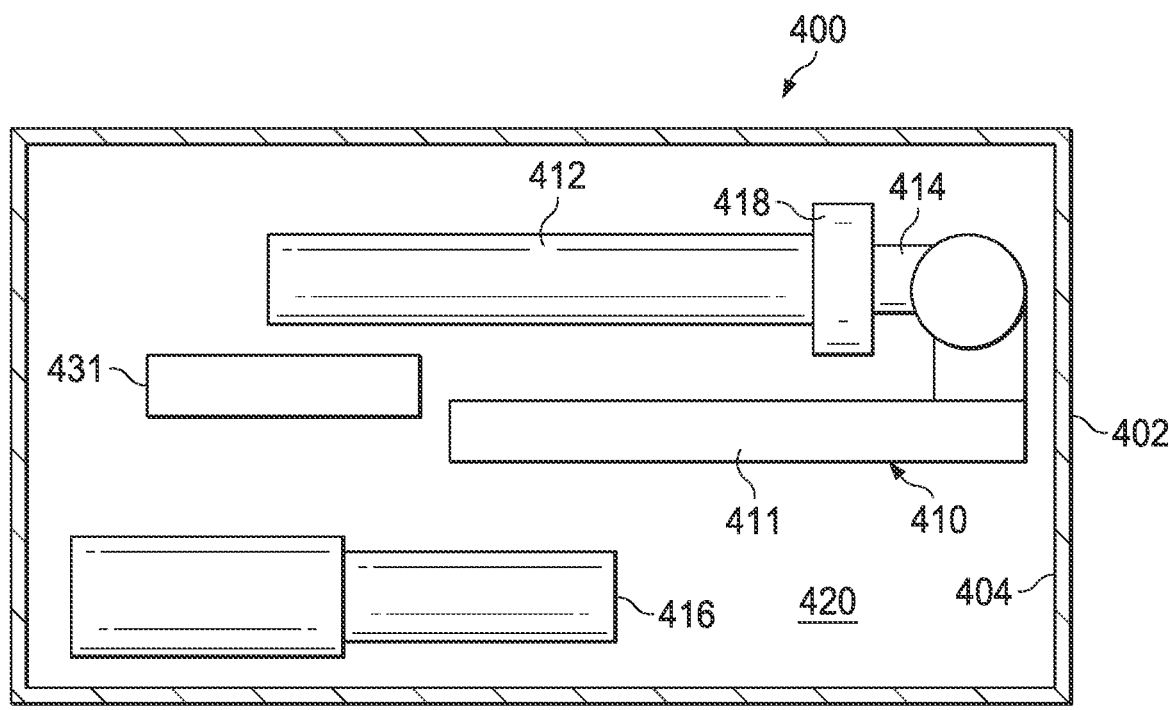
FIG. 4C is a top view of an interior of a reclosable storage container including a clamp according to some embodiments.
Figure 4D:
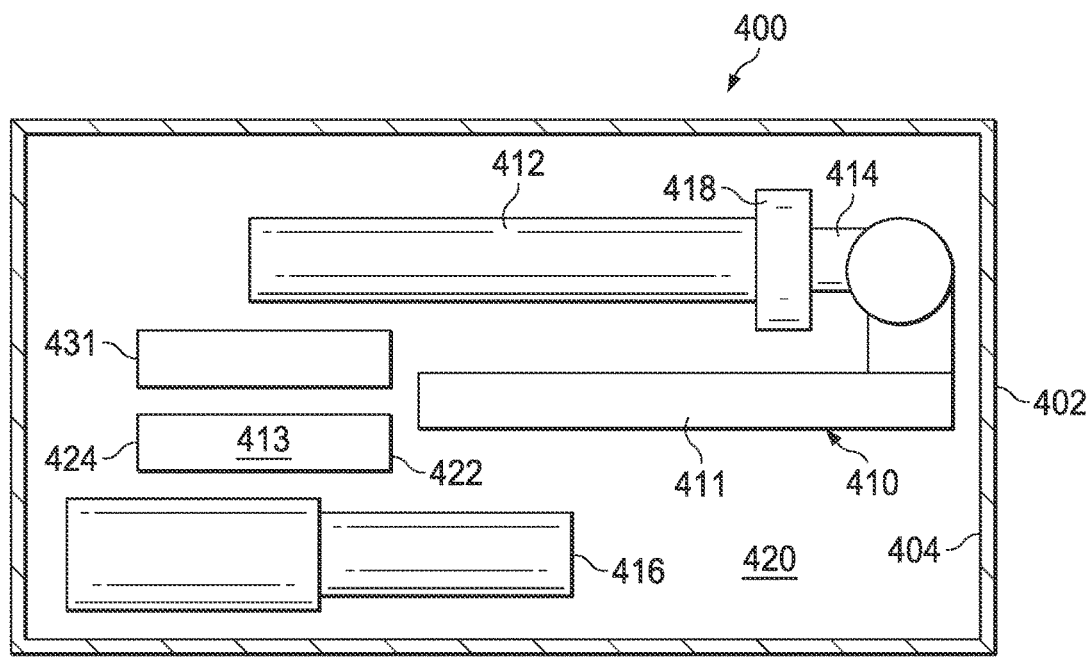
FIG. 4D is a top view of an interior of a reclosable storage container including a kinematic arm according to some embodiments.

FIG. 4B is a top view of the interior 420 of the storage container 400 including a drive unit 416 according to some embodiments. The drive unit 416 is substantially similar to the drive unit 216. FIG. 4C is a top view of the interior 420 of the storage container 400 including a clamp 431 according to some embodiments. The clamp 431 is substantially similar to the clamp 231. FIG. 4D is a top view of the interior 420 of the storage container 400 including a kinematic arm 413 according to some embodiments. As discussed above with respect to FIG. 4A, the storage container 400 is sterilized by undergoing a sterilization process in an autoclave. The drive unit 416, the clamp 431, and the kinematic arm 413 are placed in the interior 420 of the storage container 400 before the storage container 400 is inserted into the autoclave. Accordingly, the drive unit 416, the clamp 431, and the kinematic arm 413 are sterilized with the storage container 400, the interior environment 420, and the other components in the interior environment 420.

In some embodiments, the components in the interior environment 420 may be arranged in the interior environment 420 in the same configuration every time the components are placed in the storage container 400. For example, fixtures, holders, or other structures may provide dedicated locations within the interior environment 420 for each component. In alternative embodiments, there is no set configuration in which the components are arranged when they are placed in the storage container 400.

In some embodiments, when removed from the interior environment 420, the kinematic arm 413 may be coupled at an end 422 to the table T. The coupling to the table T may be direct or indirect (e.g., via the rail 209, via the clamp 431, or via another type of suitable connection). The kinematic arm 413 is coupled at an end 424 to the coupling member 418. In some embodiments, the kinematic arm 413 (which may be a support component) and the clamp 431 are coupled together to kinematically support the manipulator 410 and, therefore, the manipulator assembly 202 before, during, and/or after a surgical procedure. In alternative embodiments, the end 424 of the kinematic arm 413 may be coupled directly to the housing 412 or to the link 414.

In some embodiments, the kinematic arm 413 may be manually manipulated to adjust the position of the manipulator assembly 202. In other embodiments, the kinematic arm 413 may be remotely manipulated by teleoperational control. For example, movement of the kinematic arm 413 may be controlled by the control system 110 (see FIG. 1). The operator O may manipulate the user control system 106 (see FIG. 1), which then manipulates the kinematic arm 413 via the control system 110. The kinematic arm 413 may move the manipulator assembly 202 in any manner that is required for the surgical procedure. For example, the kinematic arm 413 may ascend, descend, translate laterally, rotate, and/or move the manipulator assembly 202 in any other direction.

Figure 4E:
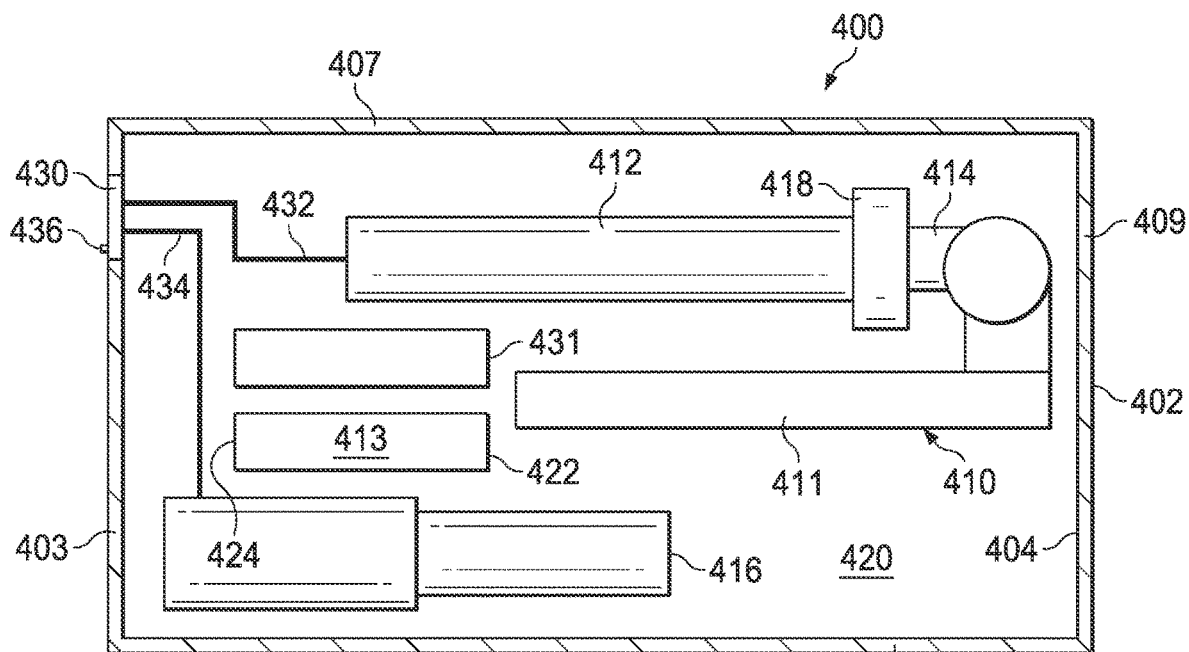
FIG. 4E is a top view of an interior of a reclosable storage container including a communication interface according to some embodiments.

FIG. 4E is a top view of the interior 420 of the storage container 400 including a communication interface 430 according to some embodiments. The communication interface 430 is substantially similar to the communication interface 330, and the outer surface 402 is substantially similar to the outer surface 302. In some embodiments, the communication interface 430 is located within the front wall 403 of the storage container 400 (e.g., between the outer surface 402 and the inner surface 404). An operator may access the communication interface 430 from the exterior (e.g., the outer surface 402) of the storage container 400. In alternative embodiments, the communication interface 430 may be partially within the front wall 403 and partially within the interior environment 420 of the storage container 400. In various other embodiments, the communication interface 430 may be partially within the front wall 403 and partially outside of the storage container 400. In some embodiments, the communication interface 430 may be partially within the front wall 403, partially within the interior environment 420, and partially outside of the storage container 400. An optional cap may be placed over the communication interface 430 before the storage container 400 is placed in the autoclave to be sterilized. The cap protects the communication interface 430 during the sterilization process and helps prevent the communication interface 430 from being damaged.

While FIG. 4E depicts the communication interface 430 in the front wall 403 of the storage container 400, it is to be understood that the communication interface 430 can be located in any other wall of the storage container 400 (e.g., a top (not shown), a bottom (not shown), the side walls 407, and/or the back wall 409). That is, the communication interface 430 establishes a way that a one- or two-way communication can be established between a device outside the storage container 400 and a sterile device inside the storage container 400 without opening the storage container 400 and without exposing the interior sterile environment 420 of the storage container 400 to the environment located outside of the storage container 400. As described in further detail below, in some embodiments, the communication interface 430 may provide electrical energy (e.g., power) to the storage container from an external source (e.g., a wall outlet, a battery, etc.). In some embodiments, there may be multiple communication interfaces placed within the walls of the storage container 400. Having multiple communication interfaces allows the operator to have easier access, via one or more communication links (e.g., communication links 432, 434), to the particular component the operator is testing within the interior environment 420 of the storage container 400. If the communication interface 430 requires a hardware connection to a device inside the storage container 400, then this connection is made prior to closing the storage container 400 and performing the sterilization process on the storage container 400 and its contents. If the communication interface 430 facilitates a wireless connection to a device inside the storage container 400, then the device inside the storage container 400 is positioned inside the storage container 400 so that the wireless connection can be established through the communication interface 430 once the storage container 400 is closed and the sterilization process is complete.

In some embodiments, communication links 432, 434 are coupled to the communication interface 430. The communication links 432, 434 may be hardware communication links providing material contact between the connected components or non-contact based communication links (e.g., electromagnetic communication links). The communication link 432 connects the manipulator 410 to the communication interface 430. Similarly, the communication link 434 connects the drive unit 416 to the communication interface 430. While FIG. 4E only depicts two communication links 432, 434, it is to be understood that more or less than two communication links may be connected to the components in the interior environment 420. For example, one communication link, three communication links, four communication links, or more than four communication links may be connected to the components in the interior environment 420. In some embodiments, a separate communication link may connect to each teleoperated component (e.g., the manipulator 410 and the drive unit 416) in the interior environment 420. In other embodiments, one communication link may simultaneously connect to each teleoperated component in the interior environment 420.

The communication links 432, 434 are used to test the components in the interior environment 420 to determine whether the components are functioning properly without opening the storage container 400 and without exposing the interior sterile environment 420 of the storage container 400 to the environment located outside of the storage container 400. In some embodiments, the communication links 432, 434 may be used to transmit communications from outside the storage container 400 via the communication interface 430 to the components in the interior environment 420. The interior components (e.g., the manipulator 410 and the drive unit 416) may be electrically powered, mechanically powered, electromechanically powered, hydraulically powered, and/or pneumatically powered. In some embodiments, the functionality of the components may be determined while maintaining sterility of the components. In some embodiments, the communication links 432, 434 are wired connections. In other embodiments, the communication links 432, 434 are wireless connections. Accordingly, the components in the interior environment 420 (e.g., the manipulator 410 and the drive unit 416) may be connected to the communication interface 430 via a wired and/or a wireless connection. In alternative embodiments, the communication links 432, 434 may be used to calibrate and/or actuate the components in the interior environment 420. In some embodiments, the communication links 432, 434 may supply power to the components in the interior environment 420. In other embodiments, the communication links 432, 434 may gather data from the components in the interior environment 420.

Regarding supplying power to the components in the interior environment 420, in some embodiments, electrical energy (e.g., power) may be provided to the storage container 400 through the communication interface 430 from an external source (e.g., a wall outlet, a battery, etc.) located external to the storage container 400. In some embodiments, the storage container 400 may contain an onboard power supply (e.g., one or more sterilizable batteries) for supplying power to the storage container 400 and the components in the interior environment 420. The onboard power supply may be located in the interior environment 420 and may undergo sterilization together with the storage container 400 and the components in the interior environment 420, for example during an autoclave sterilization process as described above. The onboard power supply may be in communication with the communication interface 430 and the components in the interior environment 420 via the communication links 432, 434. In some embodiments, the storage container 400 may receive power from an external source over the communication interface 430, from an onboard power supply, or from both an external source and the onboard power supply. The power may then be supplied to the components in the interior environment 420 via one or more of the communication links 432, 434. In some examples, the power supplied to the components stored in the container 400 may be used to power one or more active elements of the components (e.g., motors, actuators, etc.). For example, the manipulator assembly 410 may include one or more motors and/or actuators. The power supplied through the communication interface 430 may be supplied to the manipulator assembly 410 and, more specifically, may be supplied to the one or more motors and/or actuators of the manipulator assembly 410. The motor(s) and/or actuator(s) may then be tested while the manipulator assembly 410 is stored within the interior sterile environment 420. Because the power may be supplied through the communication interface 430 and the communication links 432, 434, the active components of the manipulator assembly 410 may be tested without the need to open the storage container 400 and without exposing the interior sterile environment 420 of the storage container 400 to the environment located outside of the storage container 400. Therefore, the active components of the manipulator assembly 410 may be tested within the interior sterile environment 420 while the interior sterile environment 420 remains sterile. In some embodiments, the storage container 400 may receive power from an external source over the communication interface 430 to charge an onboard power supply in the storage container 400.

In some embodiments, the communication interface 430 is a teleoperation interface used to connect with the teleoperated components (e.g., the manipulator 410, a movable component of the manipulator 410, the drive unit 416, a movable component of the drive unit 416, the kinematic arm 413, or any other teleoperated component) in the interior environment 420. In some examples, the manipulator 410 includes at least one movable component (e.g., an arm portion 411) that is actuated in response to the communication sent from the control system 110. Similarly, the drive unit 416 includes at least one movable component (e.g., a motor) that is actuated in response to the communication sent from the control system 110. Alternatively, the manipulator 410 may be a movable component that is actuated in response to the communication sent from the control system 110, and the drive unit 416 may also be a movable component that is actuated in response to the communication sent from the control system 110.

A communication may be sent from the control system 110 (see FIG. 1) to the manipulator 410, for example, via the communication link 432. In other embodiments, the communication interface 430 is a self-test interface used to instruct the manipulator 410 to perform a self-test. The manipulator 410 may then perform an internal system check to determine whether the manipulator 410 is operational. In other examples, the communication interface 430 is a component status interface used to determine an operation status of the manipulator 410. The manipulator 410 may send a communication via the communication link 432 and via the communication interface 430 indicating an operational status of the manipulator 410. In various other embodiments, the communication interface 430 may include an indicator light 436 that indicates whether the teleoperated component being tested (e.g., the manipulator 410) is functioning properly. The indicator light 436 may turn on to indicate that the manipulator 410 is functioning properly. If the manipulator 410 is not functioning properly, the indicator light 436 may remain off. In some embodiments, the indicator light 436 may change color (e.g., from red to green) to indicate that the manipulator 410 is functioning properly, and may not change color (e.g., by remaining red) to indicate that the manipulator 410 is not functioning properly. In other embodiments, the indicator light 436 may turn on as a red color to indicate that the manipulator 410 is not functioning properly.

In some embodiments, a communication sent from the control system 110 to the teleoperated components in the interior 420 of the storage container 400 via the communication interface 430 and the communication links 432, 434 commands movement of one or more of the teleoperated components in order to demonstrate the operability of the teleoperated components. The inner surface 404 of the storage container 400 may include one or more tactile interfaces (e.g., tactile interface 460). The tactile interface 460 may be a pressure pad, a switch, a button, and the like, that may be physically contacted by the manipulator 410. The tactile interface 460 may be positioned such that the manipulator 410 may physically contact the tactile interface 460. The operator may determine that the manipulator 410 is functioning properly if, after the communication is sent instructing the manipulator 410 to move, the manipulator 410 physically contacts the tactile interface 460. After the manipulator 410 physically contacts the tactile interface 460, a communication may be sent by the tactile interface 460 to the control system 110 via the communication interface 430 indicating that the manipulator 410 contacted the tactile interface 460.

In alternative embodiments, the tactile interface 460 may be positioned such that the drive unit 416 may physically contact the tactile interface 460. The operator may determine that the drive unit 416 is functioning properly if, after the communication is sent instructing the drive unit 416 to move, the drive unit 416 physically contacts the tactile interface 460. After the drive unit 416 physically contacts the tactile interface 460, a communication may be sent by the tactile interface 460 to the control system 110 via the communication interface 430 indicating that the drive unit 416 contacted the tactile interface 460.

In still other examples, the drive unit 416 may be coupled to the manipulator 410 while both components are in the interior environment 420. In such examples, a communication may be sent instructing the drive unit 416 to actuate the manipulator 410. Alternatively, a communication may be sent instructing the manipulator 410 to actuate the drive unit 416. The operator may determine that the drive unit 416 is functioning properly if, after the communication is sent, the manipulator 410 and/or the drive unit 416 physically contacts the tactile interface 460.

In some embodiments, testing of the components in the interior environment 420 may include electronic integrity testing, brake testing, and/or drive train integrity testing. In some cases where electronic integrity testing, brake testing, and drive train integrity testing are each performed, the testing may be performed in a specific order such that electronic integrity testing is performed before brake testing and brake testing is performed before drive train integrity testing. In other embodiments, electronic integrity testing, brake testing, and drive train testing may be performed simultaneously or in any other order.

The electronic integrity testing is used to test that the electronic boards (e.g., nodes) and sensors localized in the components in the interior environment 420 and their communication channels are functioning properly. Each of the nodes may be connected via an interconnected network through which each node may communicate with each other node. The electronic integrity testing may include a test of global communications, whereby the nodes send messages throughout the interconnected network to make sure all of the nodes are present and communicating. The global communication may be determined to be functioning properly if messages are being sent and received by each of the nodes. In some embodiments, the messages for the global communications test may include the nodes sending/receiving unique IDs, ping-echo queries, and the like. Additionally or alternatively, the electronic integrity testing may include a local test, whereby one or more nodes run a local diagnostic test to make sure all of the sensors connected to the one or more nodes are within a nominal range for each particular sensor. The local diagnostic test for a node may be determined to be functioning properly if all of the sensors connected to the node are reading nominal values within a predetermined range for each particular sensor. In some embodiments, the components in the interior environment 420 may include redundant sensors that may be used to check whether primary sensors in the components are functioning. The local diagnostic test described above may also test the redundant sensors connected to the node to determine whether the redundant sensor readings match the primary sensor readings within a specified error tolerance. For example, the local diagnostic test may determine that a redundant sensor is functioning properly if a reading from the redundant sensor matches a reading from the corresponding primary sensor within the specified error tolerance. Sensor status information from the local diagnostic test for a node may be part of the messages exchanged during the global communications test.

The brake testing is used to ensure that the brakes of the motorized joints of the components in the interior environment 420 are functioning properly. In more detail, a manipulator assembly (e.g., the manipulator assembly 410) may include a brake system to allow motorized joints to be locked into place. Each motorized joint may include a brake, and the brakes may be applied to hold the manipulator assembly in place. In some embodiments, when a manipulator assembly is in use, the brakes may be applied when the manipulator assembly is not being actuated, for example, or when the manipulator assembly is in a fault condition. When the brakes are applied, the joint actuators can be turned off. The brakes may have a holding requirement with an upper force limit and a lower force limit. The brake holding limits may be set such that the brakes are strong enough to hold the manipulator assembly when the joint actuators are off (e.g., to prevent the manipulator assembly from inadvertently moving), while also permitting a human operator to overpower the brake holding force (e.g., to move a faulted manipulator assembly away from an area to allow for human intervention). The brake test may test a brake of a motorized joint by leaving the brake of the joint applied while commanding a joint actuator of the motorized joint to move with a prescribed amount of force. The range of motion in which the joint may need to move for the brake test may be small. For example, the range of motion may be a few degrees in cases when the brakes of a rotary joint are being tested. During the brake test, joint friction is measured to make sure the brake holding force is between the upper force limit and the lower force limit. If it is determined that the joint moves too much, then the brake may be determined to not be sufficiently holding the joint (e.g., the brake holding force is below the lower force limit). Conversely, if it is determined that the joint moves too little, then the brake may be determined to be holding the joint with too much force (e.g., the brake holding force is above the upper force limit). A joint may be determined to pass the brake test when the joint friction is within a specified range. For example, a joint may be determined to pass the brake test when the brake holding force is between the lower force limit and the upper force limit.

In some embodiments, once the brakes have been tested, the brakes can be released and the joints can be held in place by the joint actuators. In some embodiments, the joints are driven by motors using gear heads and include two position sensors (e.g., encoders). The position sensors may be located at a motor shaft and at the joint itself (i.e., the position sensors are located before and after the gear head). During drive train testing, the manipulator assembly may be commanded to make a short motion, and the signals from the two position sensors may then be compared. The drive train testing may be used to measure gear head backlash as well as gear head friction. The drive train testing may be determined to be satisfied (i.e., it may be determined that the manipulator assembly passes the drive train testing) when the gear head backlash and the gear head friction are within a predetermined specification or tolerance and when the position sensors are functioning and their motion measurements are in agreement. The motion of the drive train integrity test may be larger than that of the brake test. For example, the range of motion may be several degrees (e.g., 10-20 degrees) in cases when the brakes of a rotary joint are being tested. The range of motion is provided for exemplary purposes only. In other embodiments, the range of motion may be less than 10 degrees (e.g., 0-10 degrees) or greater than 20 degrees (e.g., 20-180 degrees).

The manipulator 410, the drive unit 416, or any other teleoperated component in the interior 420 of the storage container 400 may be tested immediately after the storage container 400 is sterilized. The manipulator 410, for example, may additionally be tested while the storage container 400 is in storage. The manipulator 410 may further be tested in the operating room immediately before the surgical procedure is to be performed. The manipulator 410 may be tested at any other time after the sterilization process and before the surgical procedure. Because the storage container 400 is not opened during the testing, the manipulator 410 remains sterile before, during, and after the testing is performed.

Figure 4F:
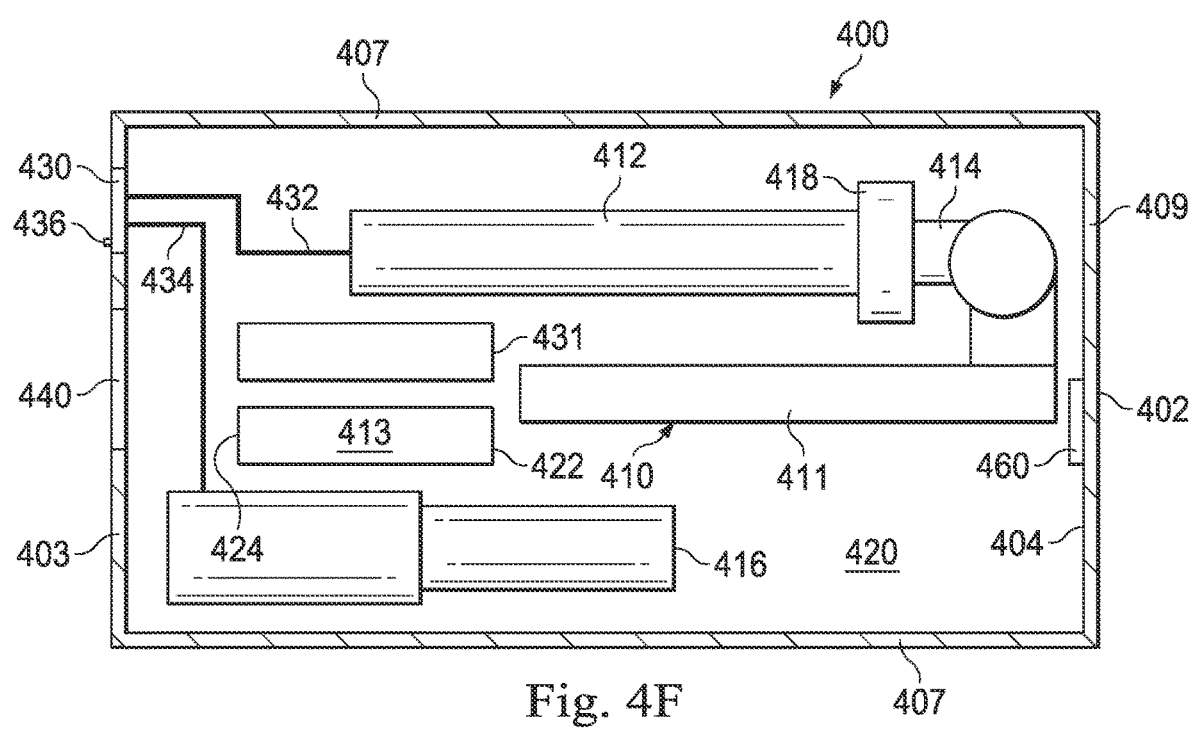
FIG. 4F is a top view of an interior of a reclosable storage container including a viewing window according to some embodiments.

FIG. 4F is a top view of the interior 420 of the storage container 400 including a viewing window 440 according to some embodiments. The viewing window 440 is substantially similar to the viewing window 340. The viewing window 440 may be transparent. In alternative embodiments, the viewing window 440 is semi-transparent. The viewing window 440 is used to view at least a portion of one or more of the components in the interior 420 of the storage container 400. For example, an operator can look through the viewing window 440 and view the components in the interior 420 of the storage container 400. In some embodiments, the operator can look through the viewing window 440 to determine whether the manipulator 410, for example, is functioning properly without opening the storage container 400. Thus, the operator can determine whether the manipulator 410 is functioning properly while maintaining sterility of the interior environment 420 of the storage container 400.

In some examples, the communication interface 430 and the viewing window 440 may be combined as one component. In such examples, an optical or infrared (IR) signal can be directed into or received from the interior 420 of the storage container 400 through the combined communication interface 430/viewing window 440. The optical or IR signal may be used to determine whether the manipulator 410, for example, is functioning properly without opening the storage container 400. The optical or IR signal may additionally or alternatively be used to determine whether the drive unit 416, for example, is functioning properly without opening the storage container 400.

The viewing window 440 is located within the front wall 403 of the storage container 400 (e.g., between the outer surface 402 and the inner surface 404). While FIG. 4F depicts the viewing window 440 in the front wall 403 of the storage container 400, it is to be understood that the viewing window 440 can be located in any other wall of the storage container 400 (e.g., a top (not shown), a bottom (not shown), the side walls 407, and/or the back wall 409). In some embodiments, there may be multiple viewing windows placed within the walls of the storage container 400. Having multiple viewing windows may provide the operator with a better line of sight to the particular component the operator is testing within the interior environment 420.

In some embodiments, a communication sent from the control system 110 to the teleoperated components in the interior environment 420 via the communication interface 430 and the communication links 432, 434 commands movement of one or more of the teleoperated components in order to demonstrate the operability of the teleoperated component(s). For example, the manipulator 410 may be actuated by the communication sent from the control system 110. In some embodiments, the operator may determine that the manipulator 410 is functioning properly if, after the communication is sent instructing the manipulator 410 to move, the operator views the manipulator 410 in motion by looking through the viewing window 440.

While the embodiments above are discussed in the context of medical or surgical procedures, it is to be understood that the systems, instruments, and methods may also be used for non-medical purposes. For example, the systems, instruments, and methods may be used for non-surgical diagnosis, industrial systems, general robotic systems, and general teleoperational systems.

Figure 5:
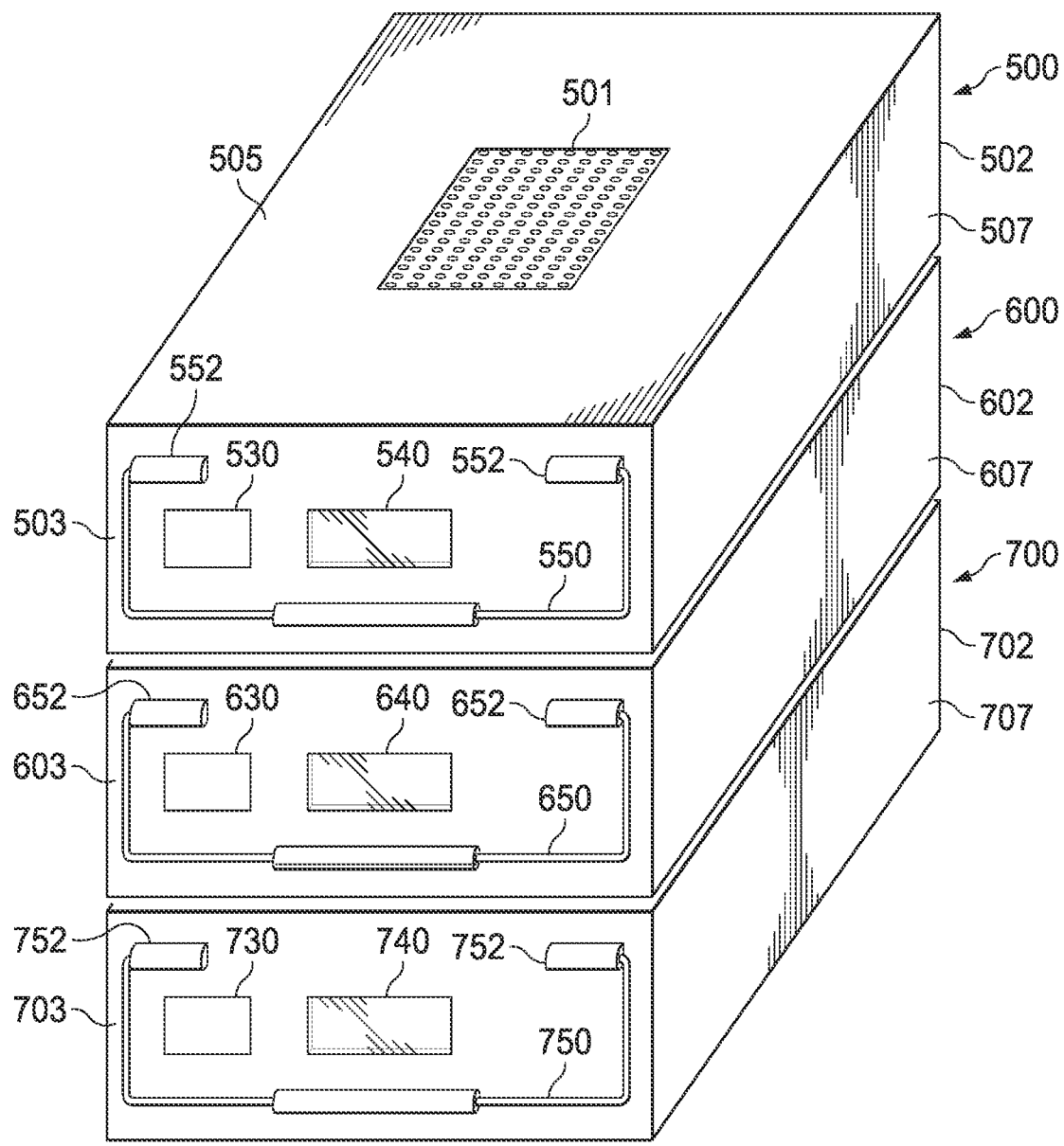
FIG. 5 is a perspective view of a stack of multiple reclosable storage containers according to some embodiments.

FIG. 5 is a perspective view of multiple storage containers 500, 600, 700 stacked on top of one another according to some embodiments. The storage containers 500, 600, 700 are each substantially similar to the storage container 300. The storage containers 500, 600, 700 may be stacked on top of each other in the operating room, in a storage room, or in any other suitable location. The storage containers 500, 600, 700 are stored after being sterilized (e.g., in an autoclave). Thus, the interiors of storage containers 500, 600, 700 and the components within the storage containers 500, 600, 700 remain sterile during non-sterile handling and while in storage in a non-sterile environment. The storage containers 500, 600, 700 may be stored in rows and/or on shelves in a storage room. The storage containers 500, 600, 700 are stacked in a manner to ensure that a front wall 503, 603, 703 of each storage container 500, 600, 700, respectively, may all be viewed by an operator at the same time. In such embodiments, communication interfaces 530, 630, 730, which are each substantially similar to the communication interface 330, may all be viewed by an operator at the same time. Similarly, the viewing windows 540, 640, 740, which are each substantially similar to the viewing window 340, may all be viewed by the operator at the same time. Such a storage configuration allows an operator to quickly and easily test and/or view the components within each storage container 500, 600, 700 without needing to unstack or move the stored storage containers 500, 600, 700.

In some embodiments, a surgical procedure may require the use of more than one teleoperated surgical manipulator assembly. In some embodiments, each of the storage containers 500, 600, 700 includes all components of a teleoperated surgical manipulator assembly (e.g., the manipulator assembly 202). In alternative embodiments, each of the storage containers 500, 600, 700 includes one type of component of a teleoperated surgical manipulator assembly. For example, the storage container 500 may only include manipulators (e.g., manipulator 410); the storage container 600 may only include drive units (e.g., drive unit 416); and the storage container 700 may only include clamps (e.g., clamp 431).

In some examples, one or more of the containers 500, 600, 700 may be connected (e.g., electrically connected) such that electrical energy (e.g., power) and/or data may be transferred between the containers 500, 600, 700. Thus, the containers 500, 600, 700 may form a local power network and/or a local data network. The connection between the containers 500, 600, 700 may be a result of the containers being stacked on top of one another. Additionally or alternatively, the connection between the containers 500, 600, 700 may be a result of the containers being in close proximity to one another. In some examples, the power and/or the data may be transferred between the containers 500, 600, 700 when only one of the containers 500, 600, 700 is connected to an external power source and/or an external data source (e.g., a data communication device). For example, the container 500 may be connected wirelessly and/or with a wired connection to an external power source (e.g., a wall outlet, a battery, etc.). The container 500 may receive power from the external power source. In this example, because the container 500 is electrically connected to one or more of the containers 600, 700, the power received from the external power source may be transferred from the container 500 to one or more of the containers 600, 700. For example, the container 500 may be in communication with an external data communication device to exchange data (e.g., send and receive data) between the data communication device and the containers 500, 600, 700. In embodiments when the container 500 receives data from an external data source, the data may be transferred from the container 500 to one or more of the containers 600, 700. In some embodiments, power and/or data may be transferred between any number of containers that are stacked on top of one another or are within close proximity to one another. In some embodiments, one container may be connected to an external power source (e.g., container 500) and a different container may be connected to an external data communication device (e.g., container 600 and/or container 700). In some embodiments where one or more of the containers 500, 600, 700 have an onboard power supply (e.g., sterilizable batteries), the local power network may be used to charge the onboard power supplies of one or more of the containers 500, 600, 700. For example, one container may be connected to an external power source (e.g., container 500), which may be used to charge onboard power supplies located in one or more of the containers 500, 600, 700 via the local power network.

Figure 6:
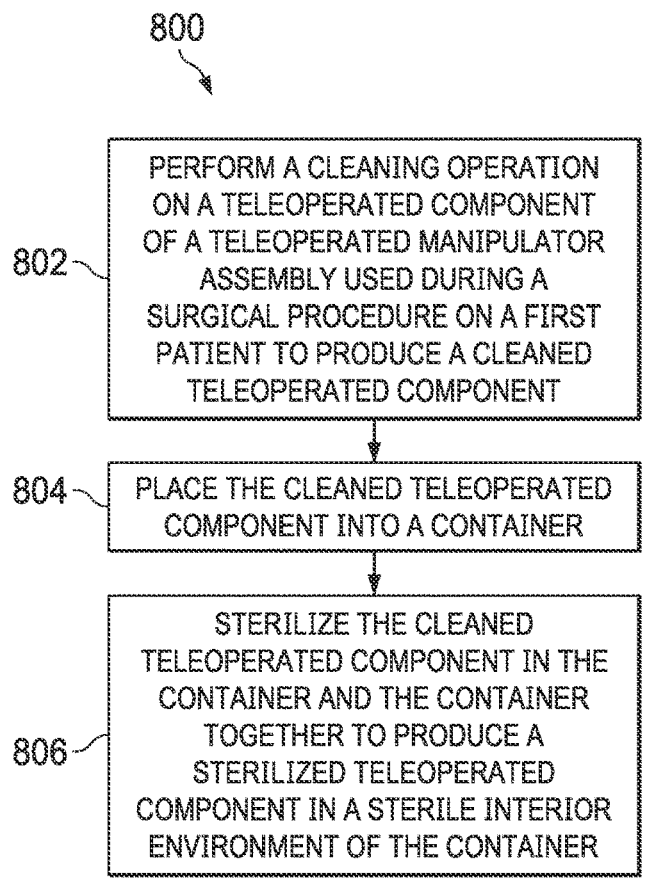
FIG. 6 illustrates a method for sterilizing a reclosable storage container according to some embodiments.

FIG. 6 illustrates a method 800 for sterilizing a storage container according to some embodiments. The method 800 is illustrated as a set of operations or processes 802 through 806 and is described with continuing reference to FIGS. 1-5. Not all of the illustrated processes 802 through 806 may be performed in all embodiments of method 800. Additionally, one or more processes that are not expressly illustrated in FIG. 6 may be included before, after, in between, or as part of the processes 802 through 806. In some embodiments, one or more of the processes 802 through 806 may be implemented, at least in part, in the form of executable code stored on non-transitory, tangible, machine-readable media that when run by one or more processors (e.g., the processors of a control system) may cause the one or more processors to perform one or more of the processes.

At a process 802, a cleaning operation is performed on a teleoperated component (e.g., manipulator 210) of a teleoperated surgical manipulator assembly (e.g., manipulator assembly 202) used during a surgical procedure on a first patient to produce a cleaned teleoperated component. The cleaning operation may be performed after the surgical procedure in a decontamination area. The cleaning operation may be performed immediately after the surgical procedure is completed. In alternative embodiments, the cleaning operation may be performed during the surgical procedure but after the teleoperated component has been used and will no longer be needed during the surgical procedure.

At a process 804, the cleaned teleoperated component is placed into a storage container (e.g., storage container 300). In some embodiments, the teleoperated component may then be connected to a communication interface (e.g., communication interface 430) via a communication link (e.g., communication link 432).

In some embodiments a filter is placed adjacent to the vent 301. In some embodiments, the filter is autoclave filter paper. The filter may be placed beneath the vent 301. For example, the filter may be placed on the side of the vent 301 that is adjacent to the interior 420 of the storage container 300. The storage container 300 may then be closed except that air and steam may pass into and out of the storage container 300 via the vent 301 and the filter.

At a process 806, the cleaned teleoperated component in the storage container 300 and the storage container 300 are sterilized together to produce a sterilized teleoperated component in a sterile interior environment of the storage container 300. In some embodiments, the teleoperated component and the storage container 300 are sterilized in an autoclave by inserting the storage container 300, with the teleoperated component inside an interior environment (e.g., interior environment 420), into the autoclave and performing a sterilization process. In embodiments in which autoclave filter paper covers the vent 301, steam may pass into the storage container 300 through the filter paper under pressure. The steam and heat destroy any microbes inside the storage container 300. The filter paper prevents microbes or other large molecules from entering through the vent 301, thus allowing the interior of the storage container 300 to remain sterilized after the sterilization process.

In alternative embodiments, e.g., when autoclave filter paper does not cover the vent 301, the storage container 300 may be closed after the cleaning process and wrapped with a sterilization wrap. The sterilization wrap may be wrapped around the exterior of the vent 301 and the storage container 300. Steam passes into the storage container 300 through the sterilization wrap under pressure. The steam and heat destroy any microbes inside the storage container 300. The sterilization wrap prevents microbes or other large molecules from entering through the vent 301, thus allowing the interior of the storage container 300 to remain sterilized after the sterilization process. The sterilization wrap may be wrapped one time, two times, or any other suitable number of times around the exterior of the vent 301 and the storage container 300.

The storage container 300 is kept closed to define a sterile interior environment (e.g., interior environment 420) of the storage container 300 that contains the sterilized teleoperated component. The sterile interior environment 420 is defined by an inner surface (e.g., inner surface 404) of the storage container 300. The sterile interior environment 420 remains sterile until the sterile interior environment 420 contacts a non-sterile object or a non-sterile environment.

In some embodiments, the method 800 may further include the process of moving the storage container 300 that contains the sterilized teleoperated component to an operating room. In some embodiments, the storage container 300 that contains the sterilized teleoperated component is moved to an operating room shortly after the sterilization process is completed. In other embodiments, the storage container 300 that contains the sterilized teleoperated component is moved to a storage room after the sterilization process is completed and is then moved from the storage room to the operating room.

The sterilized teleoperated component may be removed from the storage container 300 in the operating room. The sterilized teleoperated component may be removed prior to or during a surgical procedure on the second patient. In some embodiments, the sterile teleoperated component is assembled into a teleoperated surgical manipulator assembly (e.g., manipulator assembly 202) for use in a surgical procedure on the second patient.

In some embodiments, the method 800 may further include the process of establishing a communication through the storage container 300 that defines an interior sterile environment 420 to a sterilized teleoperated component of a teleoperated surgical manipulator assembly within the interior sterile environment 420. The communication may be established using communication links 432, 434. The communication is used to test the sterilized teleoperated component while maintaining sterility of the sterilized teleoperated component in the storage container 300. This allows an operator to determine whether the sterilized teleoperated component is functioning properly prior to removing the sterilized teleoperated component from the storage container 300, which maintains sterility of the sterilized teleoperated component. Thus, the operator can determine whether the sterilized teleoperated component is functioning properly well before the time of the surgical operation. This can allow for a replacement sterilized teleoperated component to be obtained, if needed, without delaying the surgical operation.

In some embodiments, the communication may include a teleoperation communication, and the component of the sterilized teleoperated component moves in response to the teleoperation communication. In some embodiments, the communication may provide a command to move a teleoperated component of the manipulator assembly 202. In other embodiments, the communication may include a self-test communication to allow for a self-test of the sterilized teleoperated component. In further embodiments, the communication may include a component status communication for the sterilized teleoperated component, a hardware communication, and/or a wireless communication.

In some embodiments, the processes 802 through 806 may be performed for a manipulator support component (e.g., kinematic arm 413, coupling member 418, and/or clamp 431) of the teleoperated surgical manipulator assembly. For example, a cleaning operation may be performed on a manipulator support component of the teleoperated surgical manipulator assembly used during the surgical procedure on the first patient to produce a cleaned manipulator support component. Additionally, the cleaned manipulator support component may be placed into the storage container 300, wherein the storage container 300 includes the vent 301. The filter may then be placed adjacent to the vent 301. The storage container 300 may then be closed. The cleaned manipulator support component in the storage container 300 and the storage container 300 may then be sterilized together to produce a sterilized manipulator support component. Further, the storage container 300 may be kept closed to define a sterile interior environment 420 of the storage container 300 that contains the sterilized manipulator support component. Then, the storage container 300 that contains the sterilized manipulator support component and the sterilized teleoperated component is moved to the operating room. The sterilized manipulator support component and the sterilized teleoperated component are removed from the storage container 300 at the operating room. Further, the sterile manipulator support component and the sterile teleoperated component may be assembled into the teleoperated surgical manipulator assembly for use in the surgical procedure on the second patient.

Figure 7:
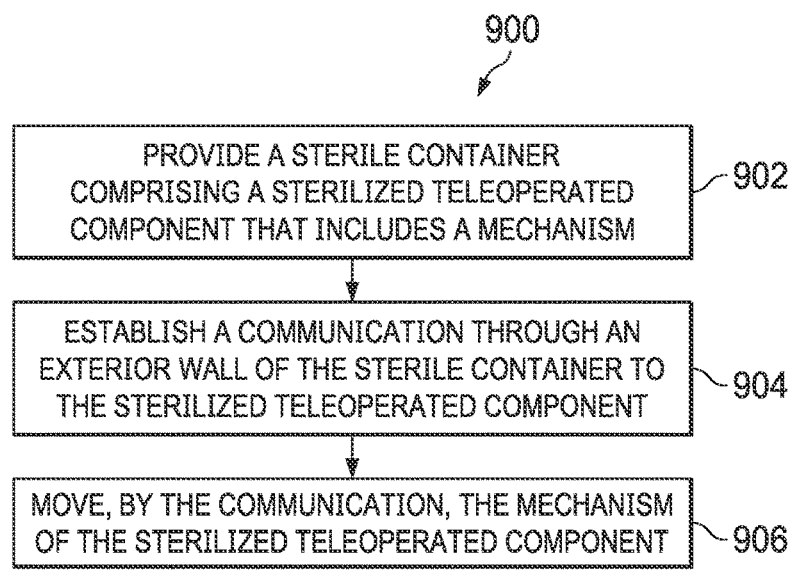
FIG. 7 illustrates a method for communicating with components in an interior of a storage container according to some embodiments.

FIG. 7 illustrates a method 900 for communicating with components in an interior of a storage container according to some embodiments. The method 900 is illustrated as a set of operations or processes 902 through 906 and is described with continuing reference to FIGS. 1-6. Not all of the illustrated processes 902 through 906 may be performed in all embodiments of method 900. Additionally, one or more processes that are not expressly illustrated in FIG. 7 may be included before, after, in between, or as part of the processes 902 through 906. In some embodiments, one or more of the processes 902 through 906 may be implemented, at least in part, in the form of executable code stored on non-transitory, tangible, machine-readable media that when run by one or more processors (e.g., the processors of a control system) may cause the one or more processors to perform one or more of the processes. In one or more embodiments, the processes 902 through 908 may be performed by the control system 110.

At a process 902, a sterile storage container (e.g., storage container 300) comprising a sterilized teleoperated component (e.g., manipulator 210) that includes a mechanism is provided. In some embodiments, the mechanism is a teleoperated arm portion (e.g., arm portion 411), a teleoperated motor, or any other suitable teleoperated mechanism. In alternative examples, the sterilized teleoperated component is the drive unit 216. In such examples, the mechanism may be one motor of a plurality of motors that manipulates a component of the instrument (e.g., the instrument 211), rather than manipulating the entire instrument.

At a process 904, a communication may be established through an exterior wall (e.g. front wall 303) of the sterile storage container 300 to the sterilized teleoperated component. The communication is established using the communication links 432, 434. In some embodiments, the communication includes a teleoperation communication that provides a command to move the mechanism of the sterilized teleoperated component. In some embodiments, the communication may provide a command to move a teleoperated component of the manipulator assembly 202. In other embodiments, the communication may include a self-test communication to allow for a self-test of the sterilized teleoperated component. In further embodiments, the communication may include a component status communication for the sterilized teleoperated component, a hardware communication, and/or a wireless communication.

At a process 906, the mechanism of the sterilized teleoperated component may optionally be moved in response to the communication. This allows an operator to determine whether the sterilized teleoperated component is functioning properly prior to removing the sterilized teleoperated component from the storage container 300, which maintains sterility of the sterilized teleoperated component. Thus, the operator can determine whether the sterilized teleoperated component is functioning properly well before the time of the surgical operation. This can allow for a replacement sterilized teleoperated component to be obtained, if needed, without delaying the surgical operation. Likewise, an electronic component may be tested to determine if the electronic component is functioning properly. The electronic component test result may generate a signal transmitted from the electronic component to a device outside the storage container 300, or it may generate a visible indication that can be seen through the viewing window 340 (e.g., a red or green light).

Optionally, a status of the sterilized teleoperated component may be analyzed. The component status may be used to ensure proper performance of the system (e.g., system 100) by indicating a correct operational status of the sterilized teleoperated component. This feature prevents a poorly functioning component from being assembled into a telesurgical system.

Optionally, the status may be communicated to at least one of medical personnel and a control system (e.g., control system 110). The status information may be received by the operator O, a surgeon, and/or any other suitable medical personnel. The status may additionally be received by a hospital information system, a patient information portal, a surgical information database, and/or any other suitable system or database. In some embodiments, the status may additionally be communicated to a manufacturer of the sterilized teleoperated component to indicate whether the sterilized teleoperated component requires maintenance.

One or more elements in embodiments of this disclosure may be implemented in software to execute on a processor of a computer system such as a control processing system. When implemented in software, the elements of the embodiments of the present disclosure are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit, a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus, and various systems may be used with programs in accordance with the teachings herein. The required structure for a variety of the systems discussed above will appear as elements in the claims. In addition, the embodiments of the present disclosure are not described with reference to any particular programming language. It will be appreciated that a variety of programming languages may be used to implement the teachings of the present disclosure as described herein.

While certain example embodiments of the present disclosure have been described and shown in the accompanying drawings, it is to be understood that such embodiments are merely illustrative of and not restrictive to the broad disclosed concepts, and that the embodiments of the present disclosure not be limited to the specific constructions and arrangements shown and described, since various other modifications may occur to those ordinarily skilled in the art.

What is claimed is:

1. A system comprising:
   a reclosable storage container comprising an interior sterile environment; and
   a sterile teleoperated component of a teleoperated surgical manipulator assembly in the interior sterile environment,
   wherein the sterile teleoperated component is configured to receive a communication in the interior sterile environment, and wherein in response to the communication, the sterile teleoperated component is configured to:
   teleoperably move in the interior sterile environment; or
   initiate a self-test in the interior sterile environment to determine an operational status of the sterile teleoperated component.

2. The system of claim 1, further comprising:
   a second sterile teleoperated component of the teleoperated surgical manipulator assembly in the interior sterile environment.

3. The system of claim 2, wherein the sterile teleoperated component and the second sterile teleoperated component couple together to teleoperate a sterile surgical instrument during surgery.

4. The system of claim 1, further comprising:
   a communication interface at an exterior surface of the reclosable storage container; and
   a communication link between the communication interface and the sterile teleoperated component.

5. The system of claim 4, wherein the communication interface comprises a teleoperation interface for the sterile teleoperated component.

6. The system of claim 4, wherein the communication interface comprises a self-test interface for the sterile teleoperated component.

7. The system of claim 4, wherein the communication interface comprises a component status interface for the sterile teleoperated component.

8. The system of claim 4, wherein the communication link comprises a hardware connection between the communication interface and the sterile teleoperated component.

9. The system of claim 4, wherein the communication link comprises a wireless connection between the communication interface and the sterile teleoperated component.

10. A method comprising:
    establishing a communication, through a reclosable storage container that defines an interior sterile environment, to a sterilized teleoperated component of a teleoperated surgical manipulator assembly within the interior sterile environment, wherein in response to the communication, the sterilized teleoperated component:
    teleoperably moves in the interior sterile environment; or
    initiates a self-test in the interior sterile environment to determine an operational status of the sterile teleoperated component.

11. The method of claim 10, wherein the communication comprises a teleoperation communication, and wherein the sterilized teleoperated component moves in response to the teleoperation communication.

12. The method of claim 10, wherein the communication comprises a self-test communication, and wherein the sterilized teleoperated component initiates the self-test in response to the self-test communication.

13. The method of claim 10, wherein the communication comprises a component status communication for the sterilized teleoperated component.

14. A system comprising:
    a closed sterile storage container;
    a sterilized teleoperated component positioned within the closed sterile storage container;
    a processor; and
    a non-transitory machine-readable medium comprising a plurality of machine-readable instructions which when executed by the processor cause the processor to perform a method comprising:
    establishing a communication through a wall of the closed sterile storage container to the sterilized teleoperated component; and
    responsive to the communication, moving a mechanism of the sterilized teleoperated component within the closed sterile storage container.

15. The system of claim 14, wherein the communication comprises a teleoperation communication, and wherein the mechanism of the sterilized teleoperated component moves in response to the teleoperation communication.

16. The system of claim 14, wherein the communication comprises a self-test communication for a self-test of the sterilized teleoperated component.

17. The system of claim 14, wherein the communication comprises a component status communication for the sterilized teleoperated component.

18. The system of claim 14, wherein the communication comprises a hardware communication.

19. The system of claim 14, wherein the communication comprises a wireless communication.

20. The system of claim 14, wherein the plurality of machine-readable instructions, when executed by the processor, further cause the processor to:
   analyze a status of the sterilized teleoperated component; and
   communicate the status to at least one of medical personnel or a control system.

\* \* \* \* \*